(12) United States Patent
Miyamura et al.

(10) Patent No.: US 8,646,316 B2
(45) Date of Patent: Feb. 11, 2014

(54) LIQUID SAMPLE QUANTITY DETERMINER

(75) Inventors: Kazuhiro Miyamura, Kyoto (JP);
Katsutoshi Ishizuka, Kyoto (JP);
Kazutaka Okamoto, Kyoto (JP)

(73) Assignee: Horiba, Ltd., Kyoto-shi (JP)

( * ) Notice: Subject to any disclaimer, the term of this patent is extended or adjusted under 35 U.S.C. 154(b) by 385 days.

(21) Appl. No.: 13/022,528

(22) Filed: Feb. 7, 2011

(65) Prior Publication Data

US 2011/0192218 A1    Aug. 11, 2011

(30) Foreign Application Priority Data

Feb. 8, 2010    (JP) ................................. 2010-025943

(51) Int. Cl.
*G01N 11/00*    (2006.01)

(52) U.S. Cl.
USPC ........................................................ 73/53.01

(58) Field of Classification Search
USPC ........................................................ 73/53.01
See application file for complete search history.

(56) References Cited

U.S. PATENT DOCUMENTS

| | | | |
|---|---|---|---|
| 4,259,291 A | 3/1981 | Smythe | |
| 4,859,422 A | 8/1989 | Qureshi et al. | |
| 6,387,328 B1 | 5/2002 | Berndtsson | |
| 7,335,339 B2 | 2/2008 | Berndtsson | |
| 7,998,437 B2 | 8/2011 | Berndt et al. | |
| 8,028,566 B2 | 10/2011 | Larsen | |
| 2009/0181463 A1 | 7/2009 | Chen | |
| 2010/0233824 A1 | 9/2010 | Verhoeckx et al. | |

FOREIGN PATENT DOCUMENTS

| | | |
|---|---|---|
| JP | 64049968 A | 2/1989 |
| JP | 01287467 A | 11/1989 |
| JP | 2000266759 A | 9/2000 |
| JP | 2002328080 A | 11/2002 |
| JP | 2004163104 A | 6/2004 |
| JP | 2005083510 A | 3/2005 |
| JP | 2005164263 A | 6/2005 |
| JP | 2005292092 A | 10/2005 |
| JP | 2007232674 A | 9/2007 |
| JP | 2008-157723 A | 7/2008 |
| JP | 2008530539 A | 8/2008 |
| JP | 2009535635 A | 10/2009 |
| WO | 9901742 A1 | 1/1999 |
| WO | 03044488 A1 | 5/2003 |
| WO | 2006018044 A1 | 2/2006 |
| WO | 2006084472 A1 | 8/2006 |
| WO | 2007125407 A1 | 11/2007 |
| WO | 2009013658 A2 | 1/2009 |

*Primary Examiner* — Peter Macchiarolo
*Assistant Examiner* — Alex Devito
(74) *Attorney, Agent, or Firm* — Alleman Hall McCoy Russell & Tuttle LLP

(57) ABSTRACT

A slide type liquid sample quantity determiner is provided that may enable the whole of a quantity determining flow path to be surely filled with a liquid sample, and also a quantity determination time to be shortened. An upstream side capillary flow path, a quantity determining capillary flow path, and a downstream side capillary flow path are reduced in diameter in this order. When a slide body is at a liquid sample quantity determination position X, an upstream side opening of the quantity determining capillary flow path is contained in a downstream side opening of the upstream side capillary flow path, and an upstream side opening of the downstream side capillary flow path is contained in a downstream side opening of the quantity determining capillary flow path.

4 Claims, 11 Drawing Sheets

LIQUID SAMPLE QUANTITY DETERMINER

TECHNICAL FIELD

The present invention relates to a slide type liquid sample quantity determiner for quantifying a liquid sample such as blood.

BACKGROUND

As described in JP 2008-157723 A, one such liquid sample quantity determiner is equipped with a rod that introduces blood into a through hole opening in its lateral circumferential surface by capillary action, and a scrape-off member that has an insertion hole having substantially the same diameter as the rod to slidably support the rod. In this quantity determiner, only by bringing blood into contact with the through hole of the rod, blood is automatically held in the through hole by capillary action. Also, this quantity determiner is one that quantifies blood on the basis of the principle that when sliding the rod relative to the scrape-off member, the scrape-off member scrapes off blood existing outside the through hole of the rod.

However, even in the case of holding the liquid sample in the whole of the through hole, it is not necessarily the case that, near the opening, the liquid sample is held so as to be completely scraped off, which becomes a factor causing quantitative error.

There is also a problem that the through hole is one that introduces a predetermined quantity of liquid sample by capillary action; however, if an inside diameter of the through hole is increased to accommodate a volume to be quantified, as a result insufficient capillary action may be obtained, and therefore it may take an undesirably long time to determine a quantity.

SUMMARY OF INVENTION

Technical Problem

The present invention aims to address the above problems, and has a main objective of, in a slide type liquid sample quantity determiner, enabling the whole of a quantity determining flow path to be surely filled with a liquid sample, and also shortening a quantity determination time.

Solution to Problem

Accordingly, a liquid sample quantity determiner according to the present invention is provided with: an instrument main body that has an upstream side capillary flow path formed in series with a liquid sample inlet, and a downstream side capillary flow path formed sandwiching a space with the upstream side capillary flow path; and a slide body that is slidably provided in the space, communicatively connecting the upstream side capillary flow path and the downstream side capillary flow path to each other, and formed with a quantity determining capillary flow path that quantifies a liquid sample introduced from the liquid sample inlet, wherein the upstream side capillary flow path, the quantity determining capillary flow path, and the downstream side capillary flow path are reduced in diameter in this order, and when the slide body is at a liquid sample quantity determination position, an upstream side opening of the quantity determining capillary flow path is contained in a downstream side opening of the upstream side capillary flow path, and an upstream side opening of the downstream side capillary flow path is contained in a downstream side opening of the quantity determining capillary flow path.

If the liquid sample quantity determiner is configured as described above, on upstream and downstream sides of the quantity determining capillary flow path, the upstream side capillary flow path and the downstream side capillary flow path are respectively formed, and the upstream side capillary flow path, quantity determining capillary flow path, and downstream side capillary flow path are reduced in diameter in this order, so that the capillary action can be enhanced toward the downstream side, and therefore the force to flow the liquid sample toward the downstream side is increased to be thereby able to surely conduct the liquid sample along the quantity determining capillary flow path. Also, when the slide body is at the liquid sample quantity determination position, the upstream side opening of the quantity determining capillary flow path is configured to be contained in the downstream side opening of the upstream side capillary flow path, and the upstream side opening of the downstream side capillary flow path is configured to be contained in the downstream side opening of the quantity determining capillary flow path, so that in the flowing process of the liquid sample, any step part expanding outside is not formed, and therefore the introduction of the liquid sample can be prevented from being blocked by surface tension acting in the step part. Further, the slide body is one that slides, and therefore it is necessary to appropriately position the upstream side capillary flow path, quantity determining capillary flow path, and downstream side capillary flow path; however, they are reduced in diameter, and therefore the positioning becomes easy.

In order to make it easy to manufacture the quantity determiner, and simply realize the above configuration, preferably, the upstream side capillary flow path, the downstream side capillary flow path, and the quantity determining capillary flow path are linear flow paths respectively having constant cross-sectional shapes, and the flow paths are formed so as to face in the same direction.

In order to verify that the liquid sample has been introduced into the quantity determining capillary flow path, preferably, on the downstream side of the downstream side capillary flow path, a liquid sensor for detecting whether or not the liquid sample has reached the quantity determining capillary flow path, is provided. If so, it can be detected by a signal from a liquid sensor that the liquid sample has reached the downstream side of the downstream side capillary flow path, and as a result, it can be verified that the liquid sample has been introduced into the quantity determining capillary flow path.

Advantageous Effects of Invention

According to the present invention configured as described, in a slide type liquid sample quantity determiner, the whole of a quantity determining flow path can be surely filled with a liquid sample, and also a quantity determination time can be shortened.

DETAILED DESCRIPTION OF THE EMBODIMENTS

One embodiment of a cell count measuring instrument serving as a measurement instrument according to the present invention will hereinafter be described with reference to the drawings.

Figure 1:
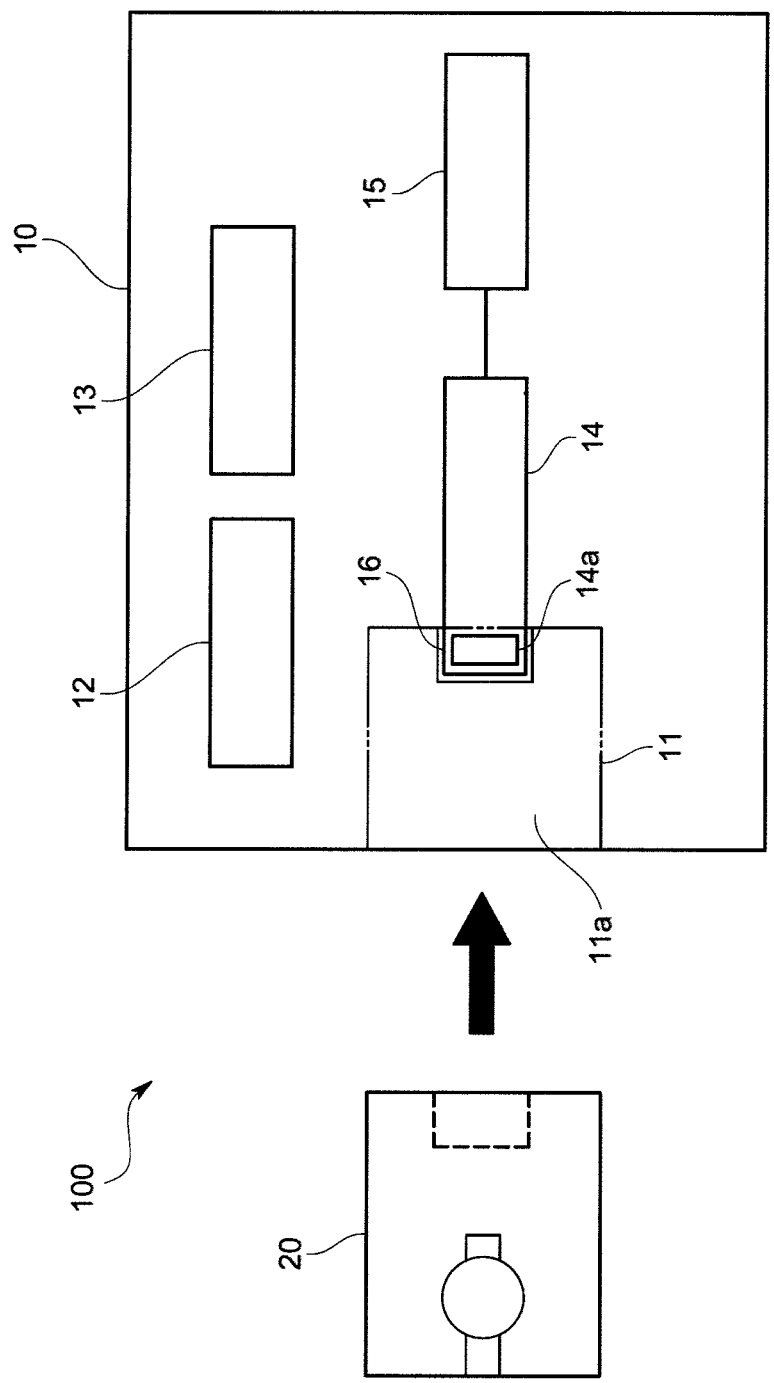
FIG. 1 is an overall schematic diagram schematically illustrating a configuration of a cell count measuring instrument of the present embodiment.
Figure 2:
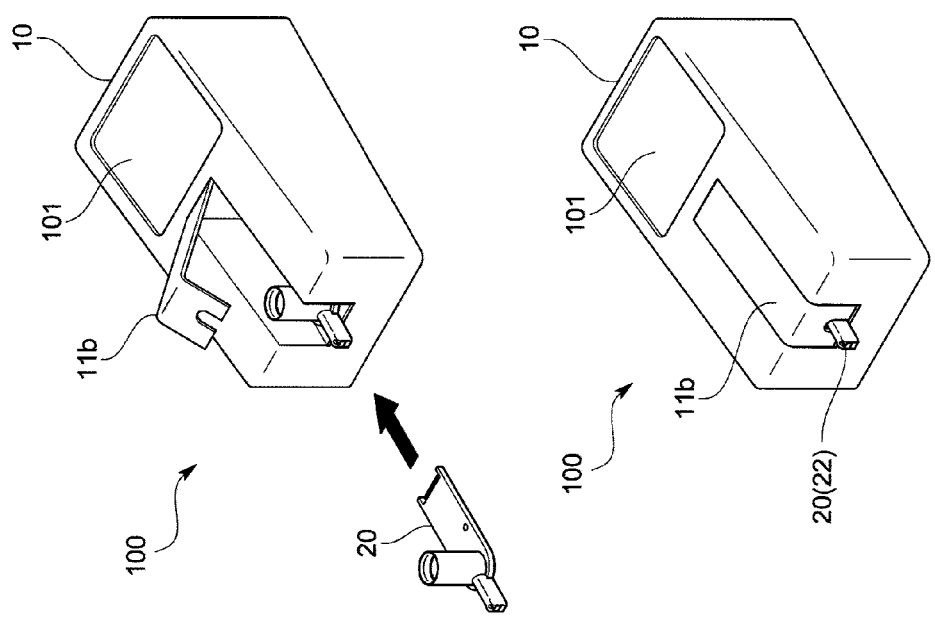
FIG. 2 is a perspective view schematically illustrating cartridge attachment in the cell count measuring instrument according to the same embodiment.

A cell count measuring instrument 100 according to the present embodiment is provided with, as illustrated in FIGS. 1 and 2, a measurement main body 10, and a cartridge 20 that is a liquid sample analyzing device detachably attached to the measurement main body 10. The measurement main body 10 is provided with: an attachment part 11 that is attached with the cartridge 20; a drive part 12 that slides a slide body 202 (to be described later) provided in the cartridge 20; a liquid supply part 13 for circulating diluted sample blood (hereinafter simply referred to as diluted blood), which serves as liquid to be measured, inside the cartridge 20; a connector part 14 for extracting a signal from the cartridge 20; and a calculation part 15 that detects the electrical signal from the connecter part 14 to calculate a cell count contained in the liquid to be measured.

The attachment part 11 is formed to be slightly larger than a width and thickness of a fore end corresponding to an insertion side end part of the cartridge 20, and is provided with a groove-like concave portion 11a (see FIG. 1) that is configured to have a predetermined depth so as to meet a shape of the insertion side end part of the cartridge 20, and a cover body 11b (see FIG. 2) that, when the cartridge 20 is inserted into the concave portion 11a, covers most of the cartridge 20 except a part (including a blood quantity determination part 22) for gripping the cartridge 20. Also, in a deep part of the concave portion 11a, a projection part 16 is formed that is to fit into a cutout part 21 (see FIGS. 3 and 4, and other drawings) formed in the fore end of the cartridge 20, and on a surface of the projection part 16, there is formed a part (conduction part 14a) of the connector part 14 that comes into contact with electrodes 28, 29, and 221 provided in the cartridge 20 to receive the electrical signal.

The drive part 12 is configured to use an engaging pawl to engage with a locking part 202a (specifically, a locking hole, see FIG. 4) provided in the slide body 202 of the cartridge 20, and a slide moving mechanism using a rack-and-pinion mechanism, motor, and the like that moves the engaging pawl in a slide direction (both not illustrated). Also, the drive part 12 is configured such that, in order to quantify blood, the slide body 202 slides between a blood quantity determination position X (see FIG. 5) and a blood introduction position Y (see FIG. 6) for mixing quantified blood with a reagent to introduce them into a mixing flow path 25 and a measuring flow path 26.

The liquid supply part 13 primarily includes a suction pump and a valve. The suction pump is configured such that, when the cartridge 20 is attached to the attachment part 11 and connected to an end point opening part H of the measuring flow path 26 (to be described later), the liquid supply part 13 depressurizes the opening part H, and provides suction to introduce the quantified blood and reagent into the mixing flow path 25 and measuring flow path 26 from a flow path inlet 24.

The connector part 14 is provided with the conduction part 14a that is electrically conducted to an inside of the concave portion 11a of the attachment part 11, such that, when the cartridge is attached, the connector part 14 comes into contact with the electrode 28 of the cartridge 20 to apply a predetermined voltage to the electrode 28, and detects, as the electrical signal, a current amount proportional to an electrical resistance generated at the time of the application. Then, the connector part 14 outputs the electrical signal to the calculation part 15 through a wiring line, such as a lead.

The calculation part 15 is provided with an electrical circuit (not illustrated) that converts the electrical signal outputted from the connector part 14 to a pulse signal to output it as a blood cell count and blood cell volume value of the diluted blood introduced into the measuring flow path 26. Then, the signal regarding the blood cell count and blood cell volume outputted in the above manner is outputted to a display 101, or the like.

Next, a detailed configuration of the cartridge 20 is described with reference to FIGS. 3 to 10.

Figure 3:
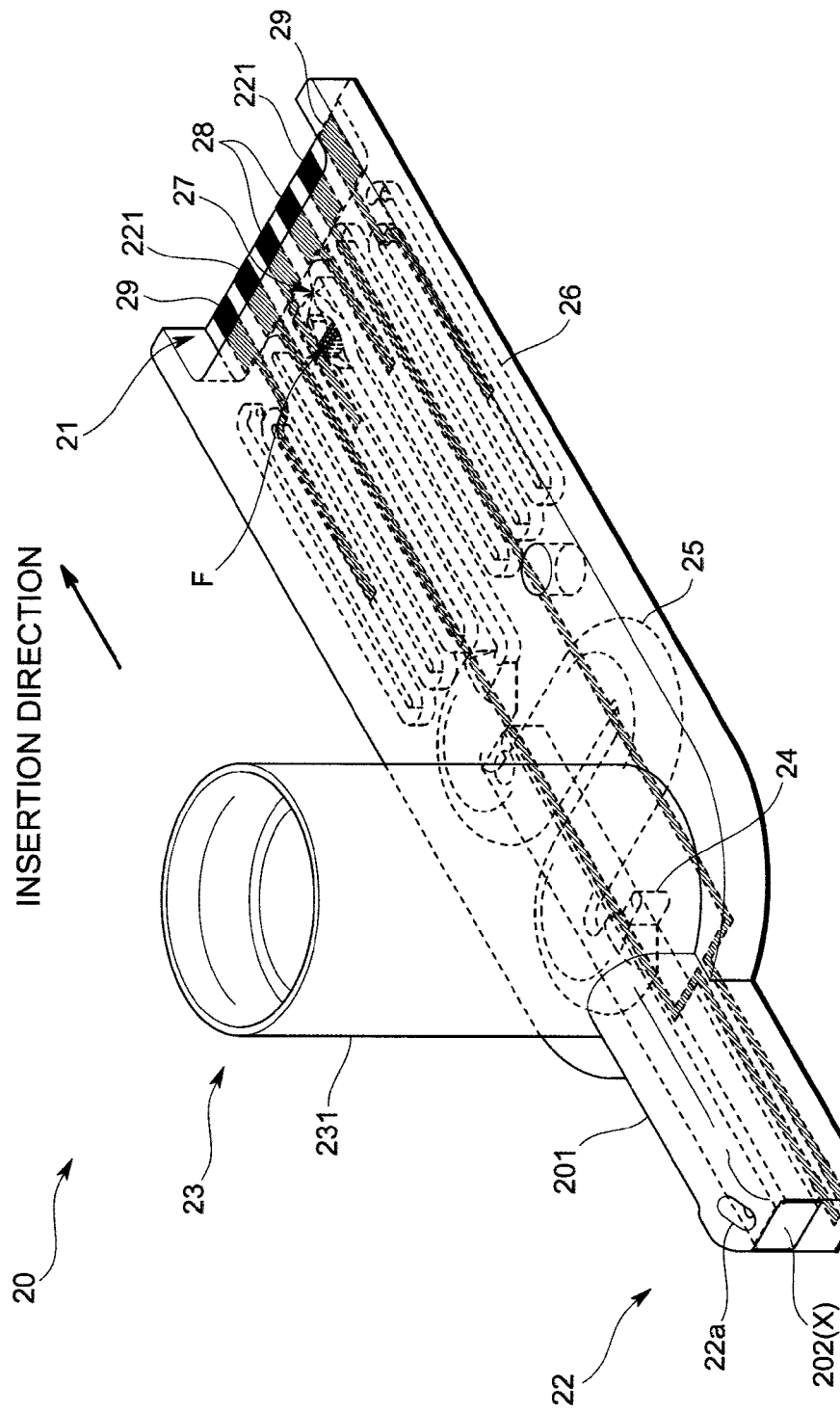
FIG. 3 is a perspective view of a cartridge according to the same embodiment.
Figure 4:
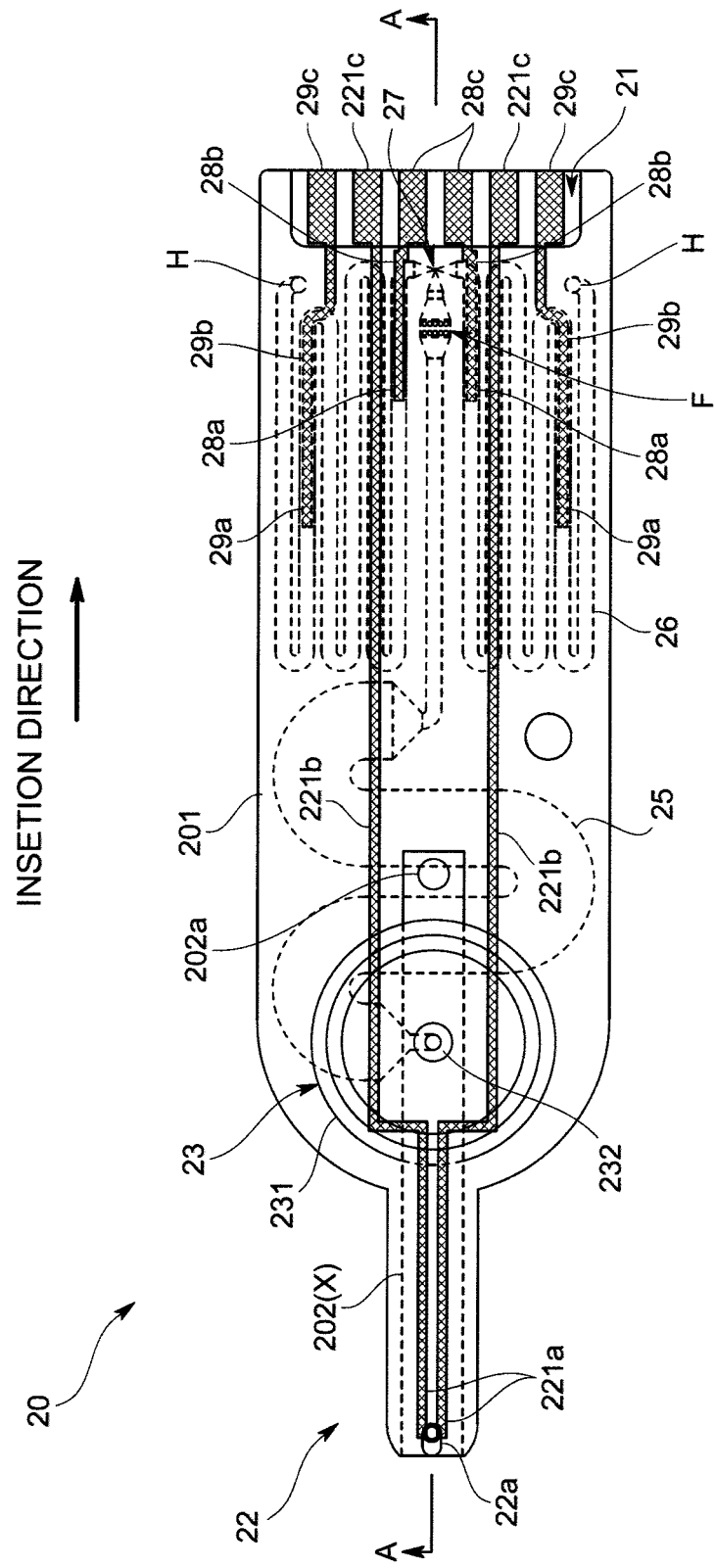
FIG. 4 is a plan view of the cartridge according to the same embodiment.

As illustrated in FIGS. 3 and 4, the cartridge 20 is essentially a one-time-use disposable cartridge, and is provided with the cutout part 21 having a substantially rectangular cross-sectional shape on the fore end side in an insertion direction thereof, and substantially near the center of an end part on a side opposite to the fore end side in the insertion direction, the blood quantity determination part 22 having a blood inlet 22a that is opened on a surface of the blood quantity determination part 22. Also, the cartridge 20 is provided with a reagent container attachment part 23 that is attached with a reagent container 3 for diluting blood quantified by the blood quantity determination part 22, a flow path inlet 24 that introduces the quantified blood and reagent, a mixing flow path 25 that is formed with and is communicatively connected to the flow path inlet 24, and a measuring flow path 26 for calculating the blood count contained in the diluted blood that is formed by the mixing through the mixing flow path 25.

Figure 5:
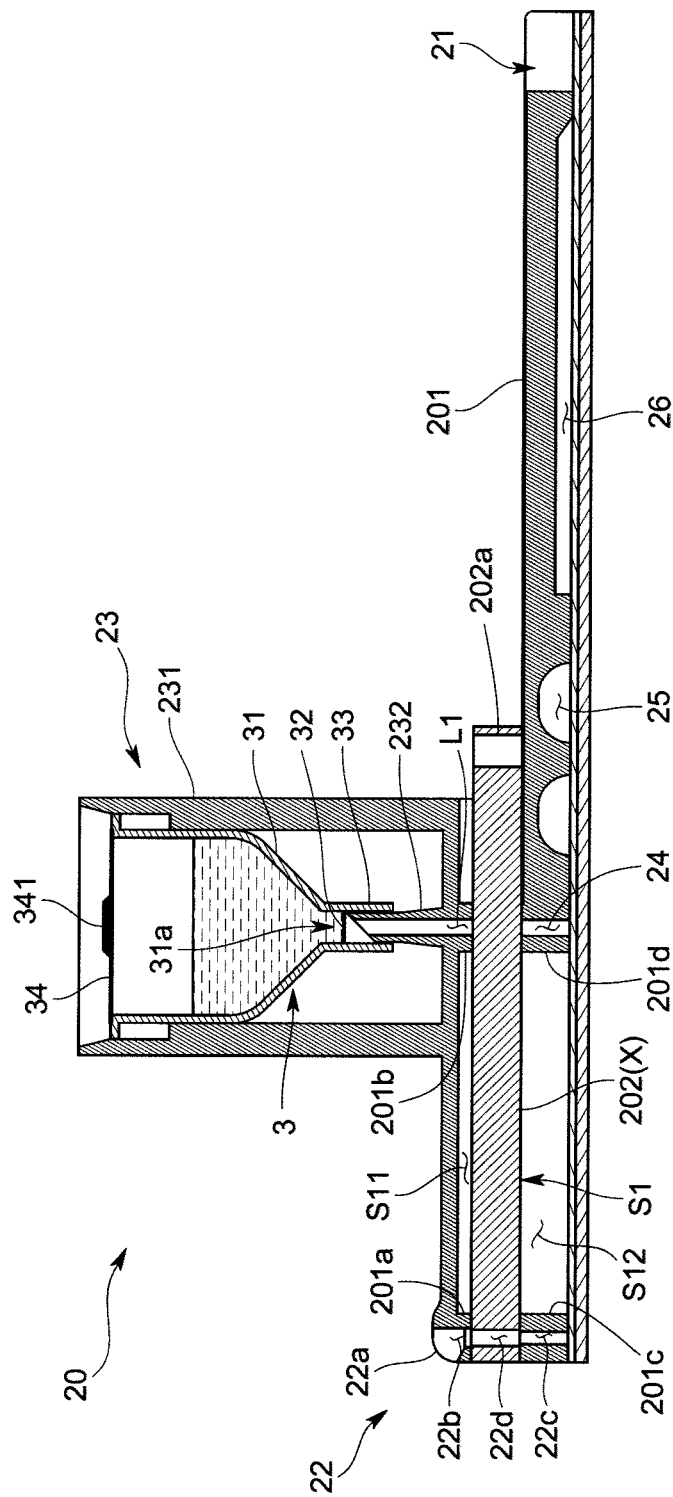
FIG. 5 is an A-A line cross-sectional view of the cartridge at a blood quantity determination position.
Figure 6:
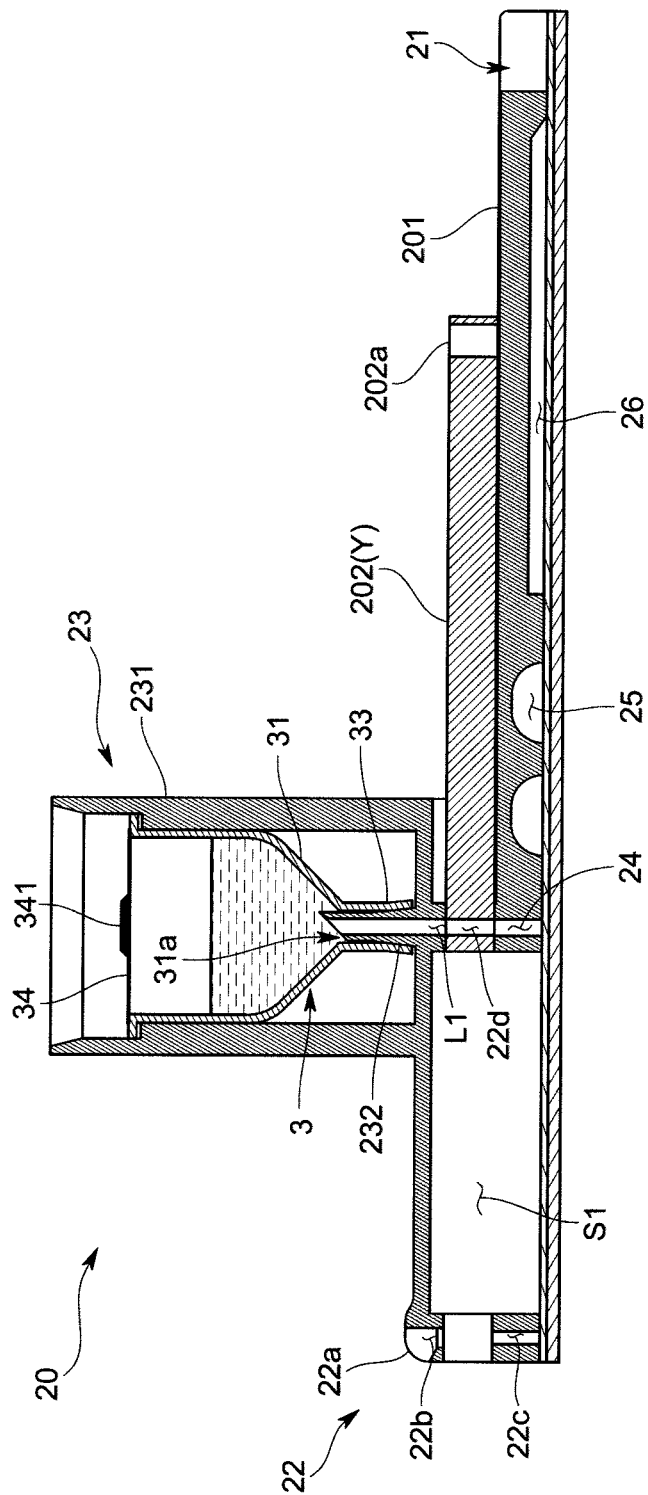
FIG. 6 is an A-A line cross-sectional view of the cartridge at a blood introduction position.

As illustrated in FIGS. 5 and 6, the blood quantity determination part 22 includes: a cartridge main body 201 having an upstream side capillary flow path 22b that is formed in series with the blood inlet 22a and a downstream side capillary flow path 22c, both of which sandwich a space 51 (space forming a slide path for the after-mentioned slide body 202), along with the upstream side capillary flow path 22b; and the slide body 202 that is slidably provided in the space 51, communicatively connects the upstream side capillary flow path 22b and the downstream side capillary flow path 22c to each other, and is formed with a quantity determining capillary flow path 22d, which quantifies blood introduced from the blood inlet 22a and has a predetermined flow path volume.

In this configuration, the engaging pawl of the drive part 12 engages with the locking part 202a formed on the insertion direction side. Via the drive part 12, the slide body 202 slides between the blood quantity determination position X (FIG. 5), wherein the quantity determining capillary flow path 22d is communicatively connected to the upstream side capillary flow path 22b and the downstream side capillary flow path 22c, and the blood introduction position Y (FIG. 6), for introducing the blood quantified by the quantity determining capillary flow path 22d and the reagent into the flow path inlet 24.

Figure 7:
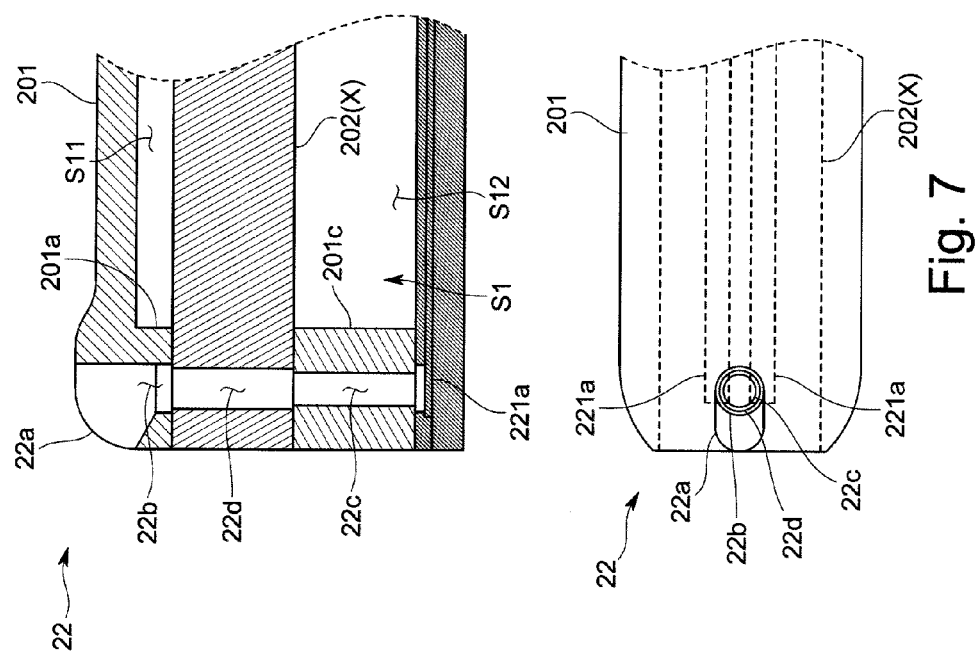
FIG. 7 is a partially enlarged cross-sectional view and a partially enlarged plan view of a blood quantity determination part according to the same embodiment.

In particular, as illustrated in an upper diagram of FIG. 7, the upstream side capillary flow path 22b, the downstream side capillary flow path 22c, and the quantity determining capillary flow path 22d are linear flow paths, respectively having constant cross-sectional circular shapes, and formed so as to face in the same direction (in the present embodiment, a vertical direction orthogonal to the insertion direction). Also, the upstream side capillary flow path 22b, quantity determining capillary flow path 22d, and downstream side capillary flow path 22c are successively reduced in diameter, in this order. That is, the quantity determining capillary flow path 22d is configured to be smaller in diameter than the upstream side capillary flow path 22b, and the downstream side capillary flow path 22c is configured to be smaller in diameter than the quantity determining capillary flow path 22d. This enables capillary forces to be enhanced toward the downstream side, and blood to be surely introduced into the quantity determining capillary flow path 22d. In addition, the upstream side of the upstream side capillary flow path 22b is of a funnel shape that increases in diameter toward the upstream side, and the blood inlet 22a, corresponding to an opening on the upstream side of the funnel shape, is configured to be a long-hole shape, and formed in a corner part of the cartridge main body 201 to open on upper and side surfaces of the cartridge main body 201. This makes it easy to introduce blood from the blood inlet 22a.

Also, as illustrated in a lower diagram of FIG. 7, the upstream side capillary flow path 22b and the downstream side capillary flow path 22c are formed concentrically in a plan view, and a downstream side opening of the upstream side capillary flow path 22b is opened to the space S1 (slide path), and an upstream side opening of the downstream side capillary flow path 22c is opened to the space S1 (slide path).

Further, when the slide body 202 is at the blood quantity determination position X, in the plan view, an upstream side opening of the quantity determining capillary flow path 22d is contained in the downstream side opening of the upstream side capillary flow path 22b, and the upstream side opening of the downstream side capillary flow path 22c is contained in a downstream side opening of the quantity determining capillary flow path 22d. In the present embodiment, when the slide body 202 is at the blood quantity determination position X, the quantity determining capillary flow path 22d is positioned concentrically with respect to the upstream side capillary flow path 22b and the downstream side capillary flow path 22c.

Note that, in order to detect that the quantity determining capillary flow path 22d is filled with blood, as illustrated in FIGS. 4 and 7, on a downstream side of the downstream side capillary flow path 22c, a liquid sensor 221 for detecting whether or not blood has reached the downstream side capillary flow path 22c, is provided. The liquid sensor 221 is configured to have electrodes, and includes: a liquid contacting part 221a that is provided so as to block all or a part of a downstream side opening of the downstream side capillary flow path 22c; a lead 221b that is drawn from the liquid contacting part 221a; and a signal extraction part 221c, which is exposed on a cartridge surface below the cutout part 21 so as to be electrically conducted to the liquid contacting part 221a through the lead 221b.

In the slide path S1, into which the slide body 202 is slidably inserted, there is formed a blood reduction preventing structure that, in the process of sliding the slide body 202 between the blood quantity determination position X and the blood introduction position Y, prevents a phenomenon in which an inner wall surface of the slide path S1 comes into contact with the upper and lower openings of the quantity determining capillary flow path 22d and quantified blood adheres to the inner wall surface, and is thereby reduced in quantity.

The blood reduction preventing structure, as illustrated in FIGS. 5 and 6, and other drawings, is provided with: an upper gap S11 that is provided between a forming wall part 201a, forming the upstream side capillary flow path 22b, and a forming wall part 201b, forming a reagent introduction path L1; and a lower gap S12 that is provided between a forming wall part 201c, forming the downstream side capillary flow path 22c, and a forming wall part 201d, forming the flow path inlet 24. Because of the configuration of the upper gap S11, the upstream side opening of the quantity determining capillary flow path 22d is configured to not come into contact with an upper wall surface of the cartridge main body 201. Similarly, because of the configuration of the lower gap S12, the downstream side opening of the quantity determining capillary flow path 22d is configured not to come into contact with a lower wall surface of the cartridge main body 201.

Also, by employing such a configuration, as illustrated in the upper diagram of FIG. 7, even if in the state where the slide body 202 is at the blood quantity determination position X, and blood introduced from the blood inlet 22a intrudes into a gap between the cartridge main body 201 and the slide body 202 (gap between the slide path S1 and the slide body 202), the intruding blood is stopped at end parts of the upper gap S11 and the lower gap S12. Therefore, the blood introduced from the blood inlet 22a can be introduced into the upstream side capillary flow path 22b, the quantity determining capillary flow path 22d, and the downstream side capillary flow path 22c without waste.

The reagent container attachment part 23 is detachably attached with the reagent container 3, serving as a liquid container for analysis, and as illustrated in FIGS. 5 and 6, is provided with: a container storage part 231 that is provided on an upper surface of the cartridge main body 201 and stores the reagent container 3; and a reagent lead-out needle 232 that is provided so as to extend from a bottom wall of the container storage part 231 and passes through a seal part 32 of the reagent container 3 stored in the container storage part 231. The reagent lead-out needle 232 is communicatively connected to the reagent introduction path L1, of which an internal flow path is opened to the space S1.

Note that the reagent container 3 is one that contains the reagent serving as a predetermined quantity of liquid for analysis, and as illustrated in FIG. 5, is provided with: a container main body 31, of which a bottom wall is formed with an opening part 31a that enables the reagent to be led out; a seal part 32 that seals the opening part 31a; and a guide part 33 that is provided outside the seal part 32 and is substantially cylindrically shaped.

The container main body 31 has a shape substantially in the form of a surface of revolution, and the bottom wall is funnel shaped. Also, the opening part 31a is formed in substantially the center of the bottom wall. Further, the guide part 33 is provided so as to cover a circumference of the seal part 32, and serves as a guide for inserting the reagent lead-out needle 232 into the seal part 32. When the reagent lead-out needle 232 is inserted into the seal part 32, the seal part 32 comes into substantially liquid-tight contact with an outer circumferential surface of the reagent lead-out needle 232.

The reagent container 3 of the present embodiment is made of resin such as polypropylene, and the container main body 31, the seal part 32, and the guide part 33 are formed by integral molding. An upper part of the reagent container 3 is opened, and after the reagent has been contained from the opening, sealed by a sealing film 34, such as an aluminum film. The sealing film 34 is provided with an atmospheric opening part 341 including, for example, a resin check valve, and simultaneously with or before the insertion of the reagent lead-out needle 232 into the seal part 32, a ventilation needle (not illustrated) is inserted to open the reagent container 3 to the atmosphere.

The guide part 33 comes into close and substantially liquid-tight contact with the outer circumferential surface of the reagent lead-out needle 232 before the reagent lead-out needle 232 is inserted into the seal part 32. Specifically, the reagent lead-out needle 232 gradually increases in diameter from a fore end toward a base end, and the guide part 33 is configured such that as the reagent lead-out needle 232 is inserted into the guide part 33, a fore end of the guide part 33 deforms as it comes into close contact with and engages with the outer circumferential surface of the reagent lead-out needle 232. Thereby, the guide part 33 comes into liquid-tight contact with the outer circumferential surface of the reagent lead-out needle 232 (see FIG. 6). That is, an inside diameter of the guide part 33 is formed to be slightly smaller than an outside diameter of the base end of the reagent lead-out needle 232. Also, an axial length of the guide part 33 is of a length long enough to, before the reagent lead-out needle 232 is inserted into the seal part 32, bring an inner circumferential surface of the guide part 33 into substantially liquid-tight contact with the whole of the outer circumferential surface of the reagent lead-out needle 232 in a circumferential direction. By providing the guide part 33 in the reagent container 3, as described, the reagent can be prevented from leaking outside the reagent container 3 at the time of or after the insertion.

The mixing flow path 25, as illustrated in FIGS. 3 and 4, is formed in series with the flow path inlet 24 opened to the slide path 51, and is also formed so as to meander in a serpentine manner inside the cartridge main body 201. The sample inlet 24 is, in the state where the slide body 202 is at the blood introduction position Y, communicatively connected to the downstream side opening of the quantity determining capillary flow path 22d (see FIG. 6). In this state, because of the suction by the liquid supply part 13, the reagent is introduced together with blood inside the quantity determining capillary flow path 22d, and into the mixing flow path 25 through the quantity determining capillary flow path 22d from the reagent introduction path L1, communicatively connected to the reagent lead-out needle 232 inserted into the reagent container 3. Then, by the suction/discharge operation of the pump of the liquid supply part 13, the quantified blood and reagent are mixed in the mixing flow path 25 to form diluted blood.

The measuring flow path 26 serving as a liquid sample flow path, as illustrated in FIGS. 3 and 4, is formed so as to be communicatively connected to a downstream side outlet of the mixing flow path 25, and configured to linearly extend from the downstream side outlet toward the fore end side so as to halve the whole of the cartridge main body 201. The measuring flow path 26 is narrowed such that inner walls facing to each other in the flow path 26 form a gap of approximately 1 mm near the cutout part 21 on the fore end side, and via the gap, an aperture part 27 is formed. Note that a size of the gap for forming the aperture part 27 can be appropriately set depending on a size of a cell to be measured (in the present embodiment, a blood cell).

Figure 8:
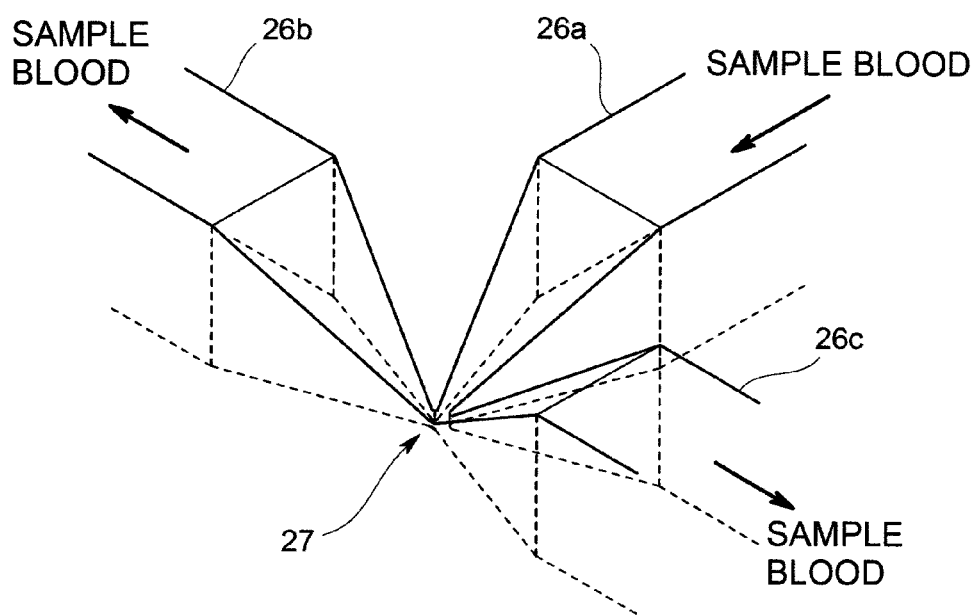
FIG. 8 is an enlarged perspective view illustrating an aperture part according to the same embodiment.

Also, the measuring flow path 26, in particular as illustrated in FIG. 8, is divided into two branches toward the downstream side from the position where the aperture part 27 is formed. Among the measuring flow paths 26 near the aperture part 27, the flow path 26a on the upstream side of the aperture part 27 is configured so as to gradually narrow a distance between the inner walls facing to each other toward the aperture part 27, and each of the flow paths 26b and 26c on the downstream side is configured so as to gradually expand a distance between inner walls facing to each other from the aperture part 27. In other areas, the flow path width is substantially constant. By forming the measuring flow path 26 as described, a flow of the diluted blood passing through the aperture part 27 is not disturbed, and blood cells contained in the diluted blood pass through the aperture part 27 in sequence.

Figure 9:
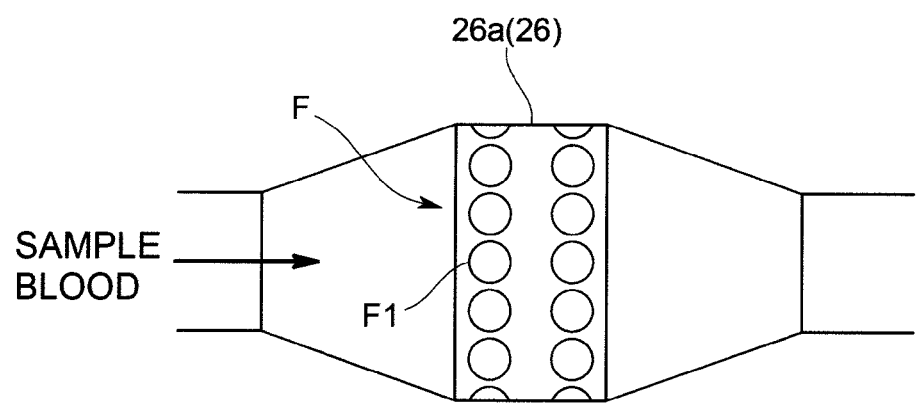
FIG. 9 is a partially enlarged cross-sectional view and a partially enlarged plan view illustrating a filter part according to the same embodiment.

Note that, on the upstream side of the aperture part 27, a filter part F is formed. The filter part F is, as illustrated in FIG. 9, formed of a plurality of columnar parts F1 that are respectively arranged at predetermined intervals. The columnar parts F1 are regularly arranged at the intervals that enable the blood cells, such as red blood cells, white blood cells, and platelets, to pass through. For example, each of the columnar parts F1 is of a cylindrical shape having a diameter of 0.3 mm, and in a direction in which the columnar parts F1 block the flow path (in a direction orthogonal to the flow path direction), the columnar parts F1 are linearly arranged at the intervals of, for example, 30 to 60 µm, and preferably 50 µm. In the present embodiment, the columnar parts F1 are arranged in two lines to form the filter part F, enabling the red blood cells (cell diameter of approximately 8 µm), white blood cells (cell diameter of approximately 10 to 20 µm), platelets (cell diameter of approximately 2 to 3 µm) and the like to pass through the filter part F, and stopping foreign substances such as dust and dirt, each having a diameter of 50 µm or more, at the filter part F. This prevents the foreign substances from reaching the electrodes 28 and 29, and therefore measurement accuracy of the blood analysis can be improved.

Turning now to describe the flow paths 26b and 26c on the downstream side of the aperture part 27, each of the flow paths 26b and 26c is formed to be slightly linear from the branch position along a fore end side of the cartridge main body 201, then bends and linearly extends toward a rear end of the cartridge, and again extends from the rear end to the fore end. By repeating this multiple times, each of the flow paths 26b and 26c is formed in a zigzag pattern (see FIG. 4). As described, the measuring flow path 26 is configured to bend multiple times at the end part side with respect to the insertion direction of the cartridge main body 201, and formed over substantially the whole area of the cartridge main body 201. This enables the measuring flow path 26 to be as long as possible within a limited area inside the cartridge main body 201. Also, the measuring flow path 26 is configured such that final end parts thereof are communicatively connected to opening parts H, opened on a surface (lower surface) of the cartridge main body 201, and the diluted blood introduced from the flow path inlet 24 travels in the measuring flow path 26 so as to push out air contained in the measuring flow path 26 from the opening parts H.

Also, as illustrated in FIG. 4, in positions on the downstream side of the aperture part 27 at the branch position of the measuring flow path 26, which are in contact with the diluted blood having passed through the aperture part 27, the pair of electrodes 28 (hereinafter also referred to as first electrodes 28) are arranged so as to sandwich the aperture part 27. Each of the first electrodes 28 includes: a liquid contacting part 28a that is formed so as to face to the inner wall of the measuring flow path 26; a lead 28b that is drawn from the liquid contacting part 28a; and a signal extraction part 28c that is exposed on the cartridge surface on the cutout part 21 so as to be electrically conducted to the liquid contacting part 28a through the lead 28b.

Also, on a downstream side of the liquid contacting part 28a in the first electrode 28, the second electrode 29 is provided. The second electrode 29 includes: a liquid detection part 29, which is provided on a downstream side where a flow path volume from the liquid contacting part 28a becomes equal to a predetermined constant volume (specifically, on an upstream side from the end point of the measuring flow path 26 by a predetermined distance); a lead 29b that is drawn from the liquid detection part 29a; and a detected signal output part 29c that is in series with an end point of the lead 29b and is provided laterally to the signal extraction part 28c, and acts as a liquid level sensor adapted to detect that the diluted blood has reached the liquid detection part 29a.

Accordingly, when the diluted blood traveling in the measuring flow path 26, after coming into contact with the liquid contacting part 28a, comes into contact with the liquid detection part 29a, an electrical signal is generated, and the electrical signal is sent to the detected signal output part 29c through the lead 29b drawn from the liquid detection part 29a, which informs the measurement main body 10 that the diluted blood has reached a predetermined reaching position in the measuring flow path 26. As described, when it is detected that the diluted blood has reached the predetermined position in the measuring flow path 26, the liquid supply part 13 stops supplying the diluted blood, and thereby the diluted blood can be prevented from reaching the opening part H at the end point of the flow path and overflowing.

Note that the signal extraction part 28c of the first electrode 28 and the detected signal output part 29c of the second electrode 29 are, as described above, arranged side by side, and configured to, when the cartridge 20 is attached to the measurement main body 10, come into electrical contact with the conduction part 14a of the connector part 14.

Figure 10:
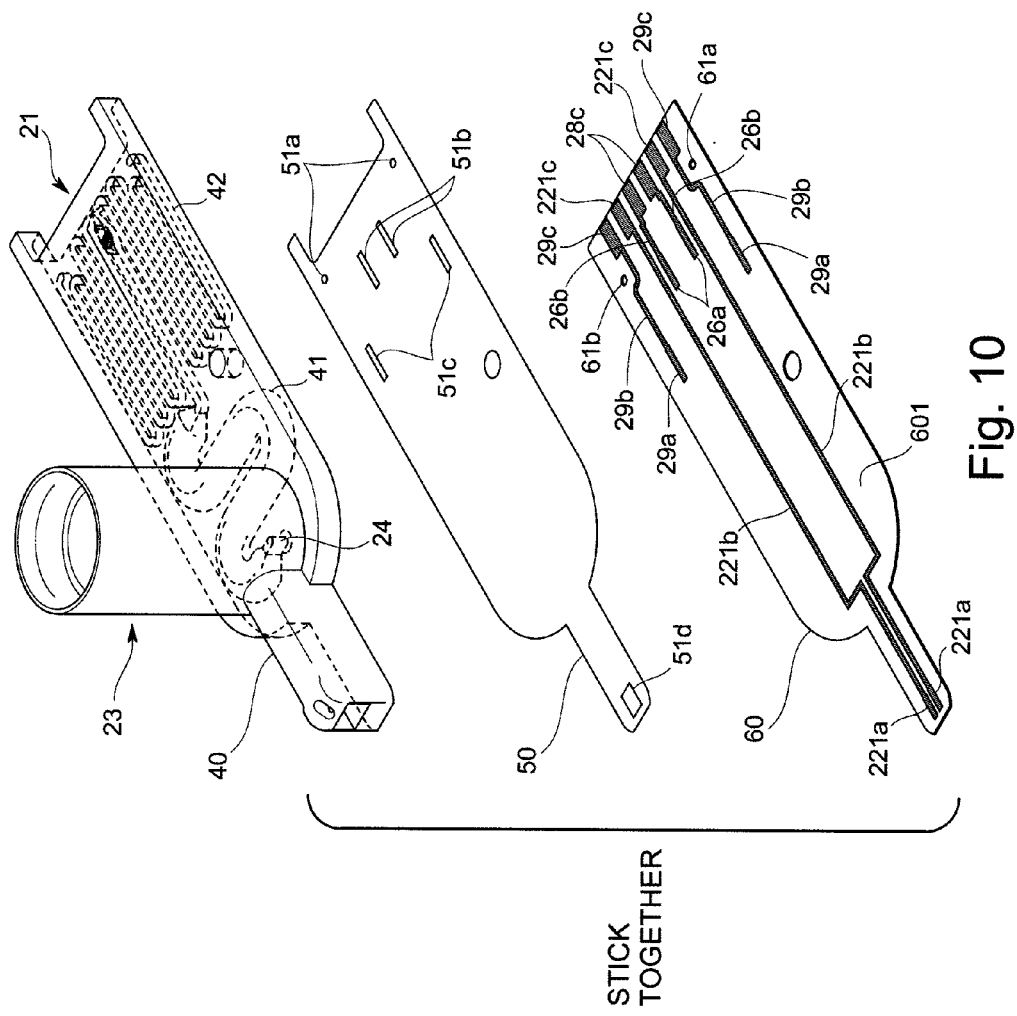
FIG. 10 is a perspective view illustrating a situation in which a cartridge main body according to the same embodiment is decomposed on a main component basis.

Next, details of an internal configuration of the cartridge main body 201 are described with reference to FIG. 10. The cartridge main body 201 includes, as illustrated in FIG. 10, a base material 40 that has a surface formed with bottom-equipped grooves 41 and 42 and is made of, for example, PMMA, and a film 60 that is adhered to the surface (lower surface) of the base material 40 via an adhesive sheet 50 and serves as a covering member made of PET.

Substantially near the center on a fore end side of the base material 40, a concave portion forming the cutout part 21 of the cartridge main body 201 is formed, and also the first bottom-equipped groove 41, forming the mixing flow path 25, and the second bottom-equipped groove 42, forming the measuring flow path 26, are formed. The first bottom-equipped groove 41 is a semicircular groove that is opened on the base material surface (lower surface) and has a width of approximately 4 mm and a depth of approximately 2 mm, and the second bottom-equipped groove 42 is a concave groove that is opened on the base material surface (lower surface) and has a width of approximately 1 mm and a depth of approximately 1 mm. Also, a start point of the first bottom-equipped groove 41 is provided by the flow path inlet 24. Corresponding to the flow path inlet 24 and through the space S1 formed inside the base material, the sample introduction path L1 and the reagent container attachment part 23 are formed respectively inside the base material and on a base material surface (upper surface on a side opposite to the surface formed with the grooves). Also, a start point of the second bottom-equipped groove 42 is in series with an end point of the first bottom-equipped groove 41. Further, as described above, near the upstream side of the position where the aperture part 27 is formed, the width of the second bottom-equipped groove 42 is gradually narrowed, and near the downstream side of the position where the aperture part 27 is formed, the width of the second bottom-equipped groove is gradually expanded. As such, bottom-equipped groove 42 and columnar parts F1 of the filter part F may be formed by any fabrication method such as micromachining fabrication, hot emboss fabrication, or optical molding, or in the case of forming the base material 40 with resin, by a method such as precision injection molding. Molding may be performed so as to form a shape preliminarily having such grooves.

Also, the film 60 is formed to have a shape that substantially coincides with the shape of the base material surface, and when adhered to the base material surface, covers opening parts of the bottom-equipped grooves 41 and 42 to thereby form the mixing flow path 25 and the measuring flow path 26, and at the positions corresponding to end points of the second bottom equipped groove 42, through-holes 61a and 61b are formed. Also, the film 60 is not provided with a cutout in a position corresponding to the cutout part 21 of the base material 40, and is configured such that when the base material 40 and the film 60 are bonded to each other, a part of the film 60 covers an upper-side of the cutout part 21. In addition, in an area covering the upper-side of the cutout part 21, the signal extraction part 28c, which is a part of the first electrode 28, the detected signal output part 29c, which is a part of the second electrode 29, and the signal extraction part 221c, which is a part of the liquid sensor 221, are formed.

Also, by applying a thin carbon coat (C) on a small amount of silver (Ag) that is coated in predetermined positions on a surface 601 of the film 60 and serves as conductive metal, the above-described first and second electrodes 28 and 29 are formed. As described above, the liquid contacting part 28a and the liquid detection part 29a, respectively constituting the electrodes, come into contact with the diluted blood flowing through the measuring flow path 26 to be thereby electrically conducted to each other, and are also electrically connected to the signal extraction part 28c and the detected signal output part 29c through the leads 28b and 29b, respectively. In addition, the liquid sensor 221 may be formed in the same manner.

Also, the first and second electrodes 28 and 29, formed on the surface 601 of the film 60, are formed by a method such as screen printing or sputtering. It should be appreciated that these electrodes can also be formed by a method other than the above-described ones, and even in a case of using a method that deposits a layer of a mixed material of silver and carbon on the whole of a back surface of the film 60, and removes or metamorphoses silver in unnecessary parts by etching or electrical treatment, these electrodes can be formed. In this case, as compared with the above-described electrodes formed by the screen printing or sputtering, the electrodes having a smaller film thickness can be formed. In addition, the liquid sensor 221 is formed in the same manner.

Also, the adhesive sheet 50 for bonding the base material 40 and the film 60 to each other is formed of a thin film-like solid adhesive that covers the whole of the surface of the base material 40, except for parts corresponding to the locations where the through-holes 61a and 61b, the liquid contacting parts 28a, the liquid detection parts 29a, and the liquid contacting parts 221a of the film 60 are formed. In FIG. 10, a reference numeral 51a represents through-holes corresponding to the through-holes 61a and 61b, 51b represents rectangular-shaped holes corresponding to the liquid contacting parts 28a, 51c represents rectangular-shaped holes corresponding to the liquid detection parts 29a, and 51d represents a rectangular-shaped hole corresponding to the liquid contacting parts 221a. The adhesive sheet 50 is solid at room temperature; however, it has a property in which when it is heated to a predetermined temperature or more, it melts to give rise to an adhesive property. By sandwiching the adhesive sheet 50 between the base material 40 and the film 60, and heating them in this state, the base material 40 and the film 60 are adapted to be bonded to each other.

Figure 11:
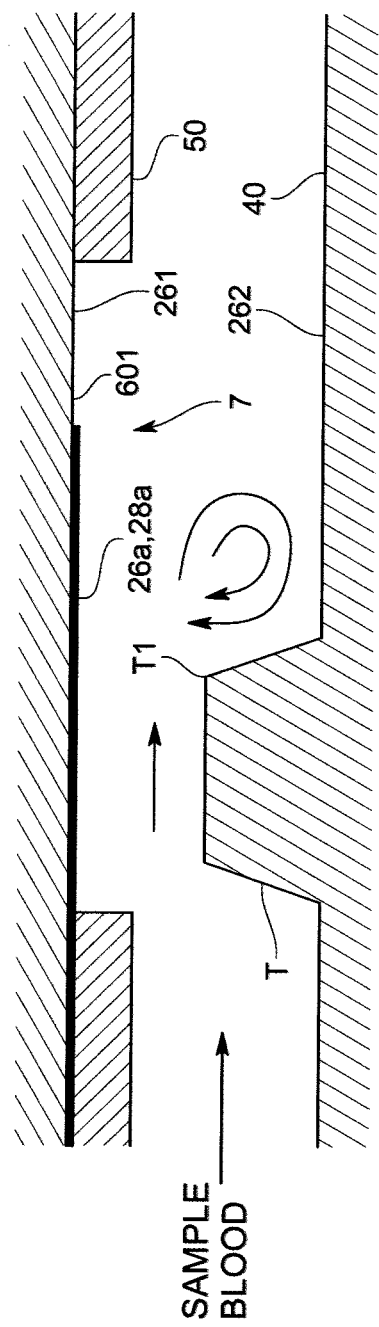
FIG. 11 is a schematic cross-sectional view illustrating the proximity of a detection part of a measuring flow path according to the same embodiment.

In the cartridge main body 201, configured as described, the liquid contacting parts 28a of the first electrodes 28 and the liquid detection parts 29a of the second electrodes that are provided on the surface 601 corresponding to an adhesion surface of the film 60 are, as illustrated in FIG. 11, configured to be contained and arranged in a stepwise concave portion 7 formed by the adhesive sheet 50 and the adhesion surface 601 of the film 60. In the present embodiment, thicknesses of the electrodes (liquid contacting parts 28a and liquid detection parts 29a) formed on the surface 601 of the film 60 are approximately 0.015 mm, and a thickness of the adhesive sheet 50 is approximately 0.1 mm, so that the electrodes (liquid contacting parts 28a and liquid detection parts 29a) are completely contained in the stepwise concave portion 7. Note that FIG. 11 illustrates an upside-down diagram.

Also, near the liquid contacting part 28a and the liquid detection part 29a in the measuring flow path 26 having substantially a rectangular cross-sectional shape of the cartridge main body 201, a projection part T is provided at a position facing to the stepwise concave portion 7.

The projection part T is one that generates a turbulent flow in the flow of the diluted blood when the diluted blood circulates on a front side of the opening of the stepwise concave portion 7. Specifically, the projection part T is formed on an inner wall surface 262 (in FIG. 11, lower surface) facing to an inner wall surface 261 (in FIG. 11, upper surface) formed with the stepwise concave portion 7 in the measuring flow path 26, and provided so as to face to the liquid contacting part 28a of the first electrode 28 and the liquid detection part 29a of the second electrode 29. The projection part T is formed over the whole area in a flow path width direction, and has a constant cross-sectional shape in the flow path width direction. That is, the projection part T is formed on a bottom surface of the bottom-equipped groove 42 of the base material 50 in the width direction. The projection part T of the present embodiment is one of which a cross-section along the flow path direction is substantially trapezoidally shaped. Also, at least a downstream side edge T1 of a top surface of the projection part T is positioned on the front side of the opening of the stepwise concave portion 7, i.e., positioned within a flow path range the stepwise concave portion 7 faces to. A position of an upstream side edge of the top surface of the projection part T is not particularly limited; however, the present embodiment illustrates the case where the upstream side edge is positioned near a downside of an upstream side end of the stepwise concave portion 7.

<Measuring Procedure>

Next, a procedure to use such a cell count measuring instrument 100 to measure a blood cell count and a blood cell size in the diluted blood serving as the liquid to be measured is described below.

First, the reagent container 3 is stored in the reagent container attachment part 23 of the cartridge main body 201. At this time, the reagent lead-out needle 232 of the reagent container attachment part 23 is not yet inserted into the seal part 32. Also, a position of the slide body 202 with respect to the cartridge main body 201 corresponds to the blood quantity determination position X. In this state, the cartridge 20 is attached to the measurement main body 10. If the cover body 11b is closed in this state, the ventilation needle provided for the cover body 11b is inserted into the atmospheric opening part 341 of the reagent container 3, and at the same time, the reagent container 3 is attached to the reagent container attachment part 23. That is, the reagent lead-out needle 232 is inserted into the seal part 32. In addition, at this time, the signal extraction parts 28c, detected signal output parts 29c, and signal extraction parts 221c formed on the surface of the cartridge main body 201 come into contact with the conduction part 14a of the connector part 14 to supply a small amount of a current so as to apply a predetermined voltage from the conduction part 14a to the liquid sensor 221, and first and second electrodes 28 and 29 of the cartridge main body 201.

Then, blood is attached to the blood inlet 22a of the cartridge main body 201, which is exposed outside the measurement main body 10. By doing so, the blood attached on the basis of capillary action by the upstream side capillary flow path 22b, quantity determining capillary flow path 22d, and downstream side capillary flow path 22c is introduced inside. At this time, the measurement main body 10 obtains a detected signal from the liquid sensor 221 provided at the downstream side opening of the downstream side capillary flow path 22c to determine whether or not the blood has reached the downstream side capillary flow path 22c. If the measurement main body 10 determines that the blood has reached the downstream side capillary flow path 22c, the measurement main body 10 slides the slide body 202 from the blood quantity determination position X to the blood introduction position Y. At this time, blood outside the quantity determining capillary flow path 22d is struck by the forming wall part forming the upstream side capillary flow path 22b and the forming wall part forming the downstream side capillary flow path 22c, and only the blood retained in the quantity determining capillary flow path 22d moves to the blood introduction position Y.

After the slide body 202 has been moved to the blood introduction position Y, the liquid supply part 13 operates to depressurize the flow path inlet 24, and thereby the blood inside the quantity determining capillary flow path 22d and the reagent are sucked into the mixing flow path 25. Then, the liquid supply part 13 performs the suction/discharge operation of the pump to thereby mix the blood and the reagent in the mixing flow path 25 and/or the reagent container 3. After the mixing, by the liquid supply part 13, the diluted blood is sucked into the measuring flow path 26.

When the diluted blood supplied into the measuring flow path 26 passes through the aperture part 27 and is branched, and the branched diluted blood flows respectively reach the pair of liquid contacting parts 28a, the connector part 14 detects an electrical resistance value between the liquid contacting parts 28a as an electrical signal through the signal extraction parts 28c. The electrical signal is a pulse signal proportional to the electrical resistance value that is varied on the basis of a blood cell count and volume (diameter) in the diluted blood passing through the aperture part 27, and the connector part 14 calculates, from the electrical signal, the blood cell count and volume in the diluted blood having passed through the aperture part 27 for a predetermined period of time (for example, a period of time from a time point when the diluted blood reaches the liquid contacting parts 28a of the first electrodes 28 to a time point when it reaches the liquid detection parts 29 of the second electrodes 29), and then outputs a result of the calculation to the display 101, or the like.

Also, when the diluted blood supplied into the measuring flow path 26 passes through the positions where the first electrode liquid contacting parts 28a are provided, and further reaches the positions where the second electrode liquid detection parts 29a are provided, an electrical resistance value between the first electrodes 28 is detected as an electrical signal through the detected signal output parts 29c and 28c. When the electrical signal is detected in the connector part 14, the calculation is stopped, and also a switching valve is operated to switch the opening parts H from the liquid supply part 13 and communicatively connect the opening parts H to the atmosphere. This returns the opening parts H to the atmospheric pressure to stop the suction of the diluted blood.

When the measurement of the blood cell count in the diluted blood is completed, as described, the cartridge 20 is detached from the attachment part 11, and the cartridge 20 containing the diluted blood is discarded according to a predetermined process, such as incineration.

EFFECTS OF PRESENT EMBODIMENT

According to the cell count measuring instrument 100 configured as described according to the present embodiment, on the upstream and downstream sides of the quantity determining capillary flow path 22d, the upstream side capillary flow path 22b and the downstream side capillary flow path 22c are respectively formed, and the upstream side capillary flow path 22b, quantity determining capillary flow path 22d, and downstream side capillary flow path 22c are reduced in diameter in this order, so that the capillary action can be enhanced toward the downstream side, and therefore force to flow blood toward the downstream side is increased to be thereby able to surely conduct the blood to the quantity determining capillary flow path 22d.

Also, when the slide body 202 is at the blood quantity determination position X, the upstream side opening of the quantity determining capillary flow path 22d is configured to be contained in the downstream side opening of the upstream side capillary flow path 22b, and the upstream side opening of the downstream side capillary flow path 22c is configured to be contained in the downstream side opening of the quantity determining capillary flow path 22d, so that in the flowing process of blood, any step part expanding outside is not formed, and therefore the introduction of the liquid sample can be prevented from being blocked by surface tension acting in the step part.

Further, the slide body 202 is one that slides, and therefore it is necessary to appropriately position the upstream side capillary flow path 22b, the quantity determining capillary flow path 22d, and the downstream side capillary flow path 22c; however, they are reduced in diameter, and therefore the positioning becomes easy.

<Other Variations>

Note that the present invention is not limited to the above-described embodiment.

For example, in the blood quantity determination part in the above-described embodiment, the upstream side capillary flow path, downstream side capillary flow path, and quantity determining capillary flow path are linear flow paths respectively having constant cross-sectional circular shapes. However, alternatively, if these paths are arranged such that, at the blood quantity determination position, the upstream side opening of the quantity determining capillary flow path is contained in the downstream side opening of the upstream side capillary flow path, and the upstream side opening of the downstream side capillary flow path is contained in the downstream side opening of the quantity determining capillary flow path, the upstream side capillary flow path, quantity determining capillary flow path, and downstream side capillary flow path may be bent paths, or paths sloping with respect to a vertical or horizontal direction.

Also, in the above-described embodiment, as the liquid sample, blood (diluted blood) is provided as an example for illustrative purposes; however, another liquid sample such as a body fluid is also applicable.

Further, the above-described embodiment discloses a cartridge of the type in which the flow path is branched at the aperture part; however, the present invention is not limited to such an embodiment, but may have an embodiment in which an aperture part is formed in a general single flow path, and wherein electrodes are arranged on upstream and downstream sides sandwiching the aperture part.

In addition, in the above-described embodiment, the second electrode provided in the flow path detects the liquid to be measured to thereby determine the timing to stop the supply of the liquid to be measured into the flow path; however, if a length or the like of the flow path formed in the cartridge is designed so as to be preliminarily known, a supply of the liquid to be measured into the flow path may be preliminarily set. In this case, without making special detection, the liquid to be measured is inhibited from overflowing from the opening part.

Furthermore, it should be appreciated that the present invention is not limited to the above-described embodiments, but can be variously modified without departing from the scope thereof.

REFERENCE CHARACTERS LIST

20: Liquid sample quantity determiner (cartridge)
22a: Liquid sample inlet (blood inlet)
S1: Space
22b: Upstream side capillary flow path
22c: Downstream side capillary flow path
201: Instrument main body (cartridge main body)
22d: Quantity determining capillary flow path
X: Liquid sample quantity determination position (blood quantity determination position)
221: Liquid sensor

The invention claimed is:
1. A liquid sample quantity determiner comprising:
an instrument main body that has an upstream side capillary flow path formed in series with a liquid sample inlet, and a downstream side capillary flow path formed sandwiching a space with the upstream side capillary flow path; and
a slide body that is slidably provided in the space, communicatively connecting the upstream side capillary flow path and the downstream side capillary flow path to each other, and formed with a quantity determining capillary flow path that quantifies a liquid sample introduced from the liquid sample inlet, wherein
the upstream side capillary flow path, the quantity determining capillary flow path, and the downstream side capillary flow path are reduced in diameter in this order, and when the slide body is at a liquid sample quantity determination position, an upstream side opening of the quantity determining capillary flow path is contained in a downstream side opening of the upstream side capillary flow path, and an upstream side opening of the downstream side capillary flow path is contained in a downstream side opening of the quantity determining capillary flow path.

2. The liquid sample quantity determiner according to claim 1, wherein the upstream side capillary flow path, the downstream side capillary flow path, and the quantity determining capillary flow path are linear flow paths each having a respective constant cross-sectional shape, and the flow paths are formed so as to be aligned in a same direction.

3. The liquid sample quantity determiner according to claim 1, wherein on a downstream side of the downstream side capillary flow path, a liquid sensor for detecting whether or not the liquid sample has reached the downstream side of the downstream side capillary flow path is provided.

4. The liquid sample quantity determiner according to claim 2, wherein on a downstream side of the downstream side capillary flow path, a liquid sensor for detecting whether or not the liquid sample has reached the downstream side of the downstream side capillary flow path is provided.

* * * * *